United States Patent [19]
Crabtree et al.

[11] Patent Number: 4,874,488
[45] Date of Patent: * Oct. 17, 1989

[54] PHOTOCHEMICAL DIMERIZATION AND FUNCTIONALIZATION OF ALKANES, ETHERS, PRIMARY AND SECONDARY ALCOHOLS, PHOSPHINE OXIDES AND SILANES

[75] Inventors: Robert H. Crabtree, Bethany; Stephen H. Brown, East Haven, both of Conn.

[73] Assignee: Yale University, New Haven, Conn.

[*] Notice: The portion of the term of this patent subsequent to Feb. 16, 2005 has been disclaimed.

[21] Appl. No.: 119,461

[22] Filed: Nov. 10, 1987

Related U.S. Application Data

[63] Continuation-in-part of Ser. No. 928,491, Nov. 10, 1986, Pat. No. 4,725,342.

[51] Int. Cl.[4] .................. B01J 19/08; C07C 2/76; C07C 29/00; C07C 31/00
[52] U.S. Cl. .................. 204/157.15; 204/157.6; 204/157.69; 204/157.9; 204/157.93; 204/157.94; 204/157.92; 204/157.95; 204/157.74; 204/158.14; 204/157.81; 204/157.73; 204/158.12; 204/157.87
[58] Field of Search .......... 204/157.15, 157.6, 157.63, 204/157.69, 157.9, 157.93, 157.94, 157.95, 157.92, 157.74, 158, 14, 157.81, 157.73, 157.87, 158.12, 905; 585/700, 703, 708, 709, 733

[56] References Cited

U.S. PATENT DOCUMENTS

| | | | |
|---|---|---|---|
| 2,636,854 | 4/1953 | Cier | 204/158.14 |
| 2,640,023 | 5/1953 | Cier | 204/157.15 |
| 2,655,474 | 10/1953 | Schutze | 204/157.15 |
| 2,657,985 | 11/1953 | Schutze | 204/157.15 |
| 2,762,768 | 9/1956 | Cier | 204/157.15 |
| 2,830,016 | 4/1958 | Cier | 204/157.15 |
| 3,154,586 | 10/1964 | Bander | 204/157.93 |
| 4,725,342 | 2/1988 | Crabtree | 204/157.9 |

Primary Examiner—John F. Niebling
Assistant Examiner—Ben C. Hsing
Attorney, Agent, or Firm—Mullen, White & Zelano

[57] ABSTRACT

The space-time yield and/or the selectivity of the photochemical dimerization of alkanes, ethers, primary and secondary alcohols, phosphine oxides and primary, secondary and tertiary silanes with Hg and U.V. light is enhanced by refluxing the substrate in the irradiated reaction zone at a temperature at which the dimer product condenses and remains condensed promptly upon its formation. Cross-dimerization of the alkanes, ethers and silanes with primary alcohols is disclosed, as is the functionalization to aldehydes of the alkanes with carbon monoxide.

24 Claims, No Drawings

PHOTOCHEMICAL DIMERIZATION AND FUNCTIONALIZATION OF ALKANES, ETHERS, PRIMARY AND SECONDARY ALCOHOLS, PHOSPHINE OXIDES AND SILANES

BACKGROUND OF THE INVENTION

This invention was made with Government support under Grant No. DE-FG02-84ER13297 awarded by the Department of Energy. The Government has certain rights in this invention.

This is a continuation-in-part of application Ser. No. 928,491, filed Nov. 10, 1986 now U.S. Pat. No. 4,725,342.

This invention relates to novel methods for the photodimerization and functionalization of various organic compounds, including alkanes, ethers, primary and secondary alcohols and silanes.

The phenomenon of $^3P_1$ Hg photosensitization of alkanes and simple oxygenated compounds has been known and studied for the better part of this century. See Steacie, E. W. R., Chem. Rev. 22, 311, 1938; Cvetanovic, R. J., Progress in Reaction Kinetics 2, pp. 39–77, 1964; Strausz, O. P., Gunning, H. E., JACS 95, 746, 1973. Such investigations have revealed that alkane, ether or methanol vapor mixed with Hg vapor and photolyzed at 254 nm. exhibit the following basic behavior:

$$R-H \xrightarrow{Hg/254} R-R + H_2 \quad [1]$$

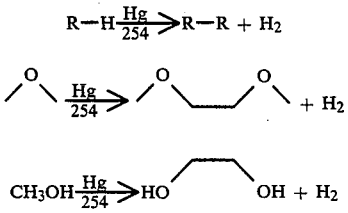

[2]

$$CH_3OH \xrightarrow{Hg/254} HO\frown OH + H_2 \quad [3]$$

The patent literature is also replete with patents relating to the photochemical production of a variety of chemical compounds. For example, U.S. Pat. No. 1,961,493 (Hillis) describes the polymerization of gaseous olefins. U.S. Pat. No. 2,636,853 (Franklin) discloses the alkylation of $C_3$ to $C_5$ paraffins with like olefins. U.S. Pat. No. 2,636,854 (Cier) discloses the production of branched paraffinic hydrocarbons from a mixture of saturated hydrocarbons. U.S. Pat. No. 2,655,474 (Schutze et al.) describes the reaction of at least two saturated hydrocarbons to form a branched product. U.S. Pat. No. 2,657,985 (Schutze et al.) also describes the production of a product comprising saturated branched chain hydrocarbons from a mixture of at least two saturated hydrocarbons. U.S. Pat. No. 2,730,495 (Gray) describes the production of alkyl and cycloalkyl hydroperoxides from a gaseous mixture of oxygen and one or more volatile paraffins or cycloparaffins. U.S. Pat. No. 2,762,768 (Cier) discloses the conversion of paraffinic hydrocarbons to a mixture of higher molecular weight hydrocarbons. U.S. Pat. No. 2,832,016 (Cier et al.) describes a reactor for conducting such a reaction. U.S. Pat. No. 2,908,622 (Bates) describes the photochemical production of formaldehyde from methane and oxygen in the presence of mercury vapor and ultraviolet light. U.S. Pat. No. 2,976,422 (Hill et al.) discloses an apparatus for irradiating chemical reactants with gamma rays, including the polymerization of paraffins and isoparaffins. U.S. Pat. No. 3,083,152 (Folkins) discloses the conversion of saturated hydrocarbons of 2 to 9 carbon atoms to the corresponding unsaturated hydrocarbons by radiation at very high temperatures. No provision for the condensation of the reaction product within the reaction zone as they are formed is contemplated by the cited references.

Other patents which illustrate the state of the art regarding photochemical processes for treating organic compounds are U.S. Pat. Nos. 2,606,867 (Pianfetti et al.); 3,203,886 (Griffin); 3,384,658 (McCracken et al.); and 3,457,154 (Lester).

The following is the general consensus found in the literature (Strausz, 1973, supra: Cramer, W. A., J. Phys. Chem., 71, 1112, 1967) for the mechanism of alkane decomposition:

$$Hg + h\nu \longrightarrow Hg^* \quad [4]$$

$$Hg^* + R-H \longrightarrow R + H + Hg \quad [5]$$

$$H + R-H \longrightarrow H_2 + R \quad [6]$$

$$2R \longrightarrow R_2 \quad [7]$$

$$2R \longrightarrow R-H + OL \quad [8]$$

$$H + OL \longrightarrow R \quad [9]$$

More recent scrutiny has shown this scheme to be overly simplistic but has agreed in principle with this earlier consensus. In his 1973 publication, Strausz states that the $^3P_1$ Hg atom sensitized decomposition of paraffins can be considered as a simple hydrogen atom transfer reaction (Strausz, 1973, supra).

This focus on a presumed free radical mechanism, the persistent adoption of the assumption that the Hg atom in this system is simply an energy transfer agent and not a catalyst, and a lack of interest in chemical synthesis caused these investigators to overlook the tremendous synthetic potential of the mercury photosensitization process. Although the patent literature describes reactions which produce products of practical utility, no reference was found in the extensive scientific literature which even mentions a potential commercial application for this process.

In our investigation of this process, we did not assume a free-radical mechanism and instead looked for signs of catalytic organometallic chemistry in this system involving R—M and M—H bonds. As a result, very persuasive evidence was accumulated which ruled out free radicals as kinetically important intermediates. At the same time, we developed the instant simple method for synthesis of countless compounds, some of which have never before been synthesized or were synthesized only with great difficulty. Central to our ability to use this system for chemical synthesis was the discovery that this mercury-substrate vapor system could select one among many different reactive molecules, based on the differences in the vapor pressures of these molecules, which phenomenon we call "differential vapor pressure selectivity." No other synthetic technique is known which operates upon this principle. One aspect of this invention is a reactor which takes full advantage of this selectivity.

However, vapor pressure selectivity alone is insufficient to make such mercury photoactivation a commercially attractive synthetic method. The excited mercury atom also exhibits site selectivity upon interaction with an individual substrate molecule. Much work is already in the literature quantifying this selectivity for alkanes as substrates. All investigators found that the order of reactivity for alkane C—H bonds is tertiary>secondary>>primary, although there is great variation in the reported magnitude of the effect. The most definitive study concluded this ratio to be 360:60:1. See Halroyd Klein, J. Phys. Chem, 67, 2277, 1963. Products of simple alkanes of six or fewer carbons were dimers and hydrogen. However, no previous workers discovered or even anticipated that the demonstrated selectivity in the assumed hydrogen abstraction step (Reaction 5) would or could lead to preferential formation at good rates of sterically strained alkanes containing adjacent quaternary carbon centers. For example, one author (H. E. Gunning, J. Chem. Phys. 22, 672, 678, 1954) said that because methylcyclopentane has only one tertiary C—H bond, one would expect that secondary radicals would predominate and that tertiary radicals would be less likely to recombine since steric factors probably would inhibit the formation of the 1,1'-dimethylbicyclopentyl. In fact, under the conditions of this invention, over forty percent of the product of this reaction is 1,1'-dimethylbicyclopentyl. Although U.S. Pat. No. 2,657,985 describes the dimerization of a 65:35 mixture of propane and isobutane in which the predominant product is 2,2,3,3-tetramethylbutane, and of a 60:40 mixture of isobutane and isopentane in which the predominant product is 2,2,3,3-tetramethylpentane, the only yield which was reported was for the latter, which was only 3.0 to 10.1% of the charge, depending on the feed rate of the reactants. In the process of this invention, much higher conversion rates and purer reaction products are obtainable.

Because the process of this invention can be conducted for prolonged periods under simple reflux conditions without adversely affecting the purity of the reaction product, this invention has made photochemical synthesis for the first time an economically feasible method of producing a variety of chemical compounds in commercial amounts. It also permits the production of chemical compounds which could not be produced or could be produced only with great difficulty by chemical synthetic routes.

OBJECTS OF THE INVENTION

It is an object of this invention to provide an improved process for the photosensitized dimerization of alkanes, ethers and alcohols.

Another object is the provision of a novel process for the functionalization of saturated hydrocarbons and ethers.

A further object is to provide a method of regulating the composition of the reaction product produced by the photosensitized dimerization or functionalization of saturated hydrocarbons.

Still another object is the provision of a novel one-step method for the production of aldehydes.

A still further object is the provision of a novel one-step method for the synthesis of disilanes.

Yet another object is the provision of a novel method for the halogenation of saturated hydrocarbons and their ethers and/or their conversion to alcohols and ketones.

Other objects will be apparent to those skilled in the art to which this invention pertains.

SUMMARY OF THE INVENTION

In one process aspect, this invention relates to a method of improving at least one of the selectivity and space-time reaction rate of a Group IIB photosensitized vapor phase dimerization of a saturated hydrocarbon, a saturated hydrocarbon ether, a saturated hydrocarbon primary or secondary alcohol, or a mixture thereof, which comprises conducting the dimerization at a reaction temperature at which the reaction product condenses immediately upon the formation thereof, preferably substantially simultaneously therewith, and remains condensed while exposed to the photosensitizing radiant energy.

In another process aspect, this invention relates to a method of enhancing the formation of tertiary-tertiary dimers in the vapor phase photosensitized dimerization of branched chain saturated hydrocarbons by the breaking of a tertiary (3°) C—H bond in both components to form a C—C bond and $H_2$, which comprises conducting the dimerization thereof according to the method of this invention while in admixture with a non-reactive gas. In a preferred embodiment of this aspect of the invention, the non-reactive gas is $H_2O$.

In still another process aspect, this invention relates to a method for the hydroxyalkylation of a volatilizable saturated hydrocarbon or an ether thereof, which comprises subjecting a gaseous mixture of the hydrocarbon or ether thereof, an alkanol and a Group IIB metal, to an amount of radiant energy comprising a frequency which can be absorbed by the metal at its ground state effective to condense the alkanol with the hydrocarbon.

In a further process aspect, this invention relates to a method for the production of an alkyldisilane which comprises irradiating a gaseous mixture of a volatilizable alkyl, dialkyl or trialkylsilane of the formula $R_1SiH_3$, $R_1R_2SiH_2$ or $R_1R_2R_3SiH$ wherein each of $R_1$, $R_2$ and $R_3$ is alkyl, e.g., of 1–6 carbon atoms, and a Group IIB metal to an amount of radiant energy comprising a frequency which can be absorbed by the metal at its ground state effective to dimerize the silane.

In a still further process aspect, this invention relates to a method for the production of a di(alkylphosphino)-ethane dioxide, which comprises irradiating a gaseous mixture of a volatilizable trialkylphosphine oxide, wherein at least one of the alkyl groups has a hydrogen atom on the carbon atom thereof alpha to the phosphorous atom, and a Group IIB metal with an amount of radiant energy comprising a frequency which can be absorbed by the metal at its ground state effective to dimerize the phosphine oxide.

In a composition aspect, this invention relates to novel compounds and mixtures of compounds produced according to the process of the invention.

In still another process aspect, this invention relates to a method for the production of fluorinated glycols which comprises irradiating a gaseous mixture of a volatilizable fluorinated alcohol, e.g., of the formula $R_1CH_2OH$ where $R_1$ is a fluoroalkyl, preferably perfluoroalkyl group, e.g., of 1–4 carbon atoms, and a Group IIB metal, to an amount of radiant energy comprising a frequency which can be absorbed by the metal at its ground state effective to dimerize the fluoroalcohol to the corresponding glycol, e.g., of the formula $R_1CHOHCHOHR_1$.

In yet another aspect, this invention relates to a method which comprises dimerizing a gaseous mixture of a Group IIB metal, a saturated hydrocarbon or ether thereof and 1,3,5-trioxane and the reaction product comprises a cross-dimer of 1,3,5-trioxane and the saturated hydrocarbon or ether thereof.

In yet another aspect, this invention relates to a method which comprises dimerizing a gaseous mixture of a Group IIB metal, a saturated amine and 1,3,5-trioxane and the reaction product comprises a cross-dimer of 1,3,5-trioxane and the saturated amine.

DETAILED DESCRIPTION

Although the photosensitized dimerization of alkanes, ethers and alcohols has been known in the prior art for many years, the space-time yields obtainable did not make this reaction a viable method for the commercial production of the products of such reactions. Also, the products were complex mixtures whose composition for all practical purposes could not be controlled.

The system employed in the process of this invention differs from that employed in the prior art in a very important aspect, viz., in the instant process the reaction product does not remain in the vapor phase through the reaction zone. Rather, condensation of the product occurs at once, usually inside the reaction zone. This immediate condensation of reaction product leads to product of higher purity. For example, the prior art obtains olefins (U.S. Pat. No. 2,655,474, col. 4, line 30, Table II) to the extent of 5–14%. The instant process produces less than 1%. Secondly, trimers are also obtained (U.S. Pat. No. 2,655,474, col. 4, lines 10 and 17), such as $C_{12}$ from $C_4$, and especially 17% of 2,2,3,3,4-pentamethylpentane (a trimer) from propane and isobutane (U.S. Pat. No. 2,657,985, col. 5, Table at bottom). Less than 3% trimer is produced in the instant process under ordinary conditions. The reason that these two products (olefins and trimers) are formed in the prior art process is that the reaction products stay in the vapor phase and are acted upon a second time by the mercury in the '985 system.

The present invention not only makes the production of such dimers by photochemical synthesis commercially feasible, it also provides novel methods for functionalization of saturated hydrocarbons and ethers thereof. Also, the product distribution from alkane substrates can be dramatically altered by simple perturbations of the conditions in accordance with this invention. In certain cases, changes greater than an order of magnitude are observed. The probable cause of this effect is most likely due to the conversion of $^3P_1$ Hg to another metastable state, $^3P_0$, which is less reactive and more selective, before reaction with the organic substrate.

Although it was reported in the prior art that alkanes, methanol, and simple ethers can be separately polymerized in the vapor phase, no attempt to functionalize an alkane by cross-dimerizing (condensing) it with an alcohol has been reported. We have found that alkanes can be selectively cross-dimerized in the process of this invention at their tertiary C—H centers with methanol, ethanol, isopropanol and like primary and secondary alkanols to convert the alkanes to the corresponding cross-dimerized alcohols. Thus, this invention can be employed to homogeneously functionalize alkanes in unlimited quantities with unlimited turnovers. We have discovered that in the case of oxygenated molecules, e.g., primary and secondary alcohols and aliphatic and cycloaliphatic ethers, the reaction always occurs at the carbon atom alpha to the oxygen. In the case of heteroalkanes, e.g., alkylmetals and dialkyl and trialkylsilanes, the condensation occurs at the heteroatom thereby joining two heteroatoms by a direct bond, by increasing the valence state of the heteroatom.

In carrying out the process of this invention, a mixture of the reactant or reactants and a Group IIB metal in the vapor state is irradiated in an otherwise conventional manner (see the prior art cited above) with radiant energy comprising a frequency which can be absorbed by the Group IIB metal at its ground state. See, e.g., U.S. Pat. Nos. 2,636,853 and 2,657,985. Hg is the metal of choice, although at high reaction temperatures which tend to produce too high a concentration thereof in the reaction zone and thereby absorb too much of the radiant energy, less volatile metals, e.g., Zn or Cd, can be employed, but the appropriate wavelength of resonance radiation must then be used. The ratio of reactant or reactants to the Group IIB metal is not critical, as very little of the metal is required to initiate and maintain the reaction. The metal can be mixed with the starting reactant or reactants in the liquid or vapor phase prior to entering the reaction zone or a supply of the metal can be maintained in the reaction zone by other means.

When a non-reactive gas is used to dilute the reactant vapors in the reaction zone, thereby enhancing 3°—3° dimer formation, the molar ratio thereof in the vapor phase can vary widely, e.g., from about 1:10 to about 100:1. As would be apparent, the space-time yield will ultimately be adversely affected by a high concentration of non-reactive gas in the reaction zone.

Similarly, when a mixture of reactants is employed, e.g., alkane and ether, alkane and alcohol, or ether and alcohol, their vapor phase molar ratio also can vary widely, e.g., from about 1:100 to about 100:1. As would be obvious, when one of the reactants is present in a low molar ratio relative to the other reactant, the dimer of the other reactant usually is the predominant reaction product. This molar ratio can be varied by varying the molar ratio of the starting reaction zone. When one reactant has a much higher boiling point than another, the molar ratio can be varied by passing a gaseous stream of the lower boiling reactant below the surface of the refluxing higher boiling reactant at varying rates.

The process of this invention can also be employed to produce aldehydes in one step from alkanes (and from ethers and alcohols as well) and carbon monoxide, and in two steps by cross-dimerization with 1,3,5-trioxolane followed by hydrolysis and to dimerize silanes.

The reaction temperature which should be employed is that which will maintain starting substrate in the vapor state within the irradiated zone of the reactor, while still permitting reaction product to condense promptly upon formation thereof and remain condensed thereafter while exposed to the radiation. By so doing, the reaction rate or the selectivity of the reaction, or both, is enhanced.

Although in a batch reaction the condensed reaction product is ordinarily permitted to return to the heated portion of the reactor and mix with the unreacted substrate, the process can be conducted continuously by fitting the reactor with a fractional distillation column which removes condensed reaction product from the reactor while permitting condensed substrate to flow downwardly back into the heated portion of the reactor or by the use of a diverter plate which diverts out of the reactor condensed product flowing down the walls of the reactor, at a point thereat which is maintained above the boiling point of the substrate. By replacing starting substrate as it is consumed and withdrawing reaction product as it is formed, and occasionally replenishing the Hg, the reaction can be conducted continuously. By passing a continuous stream of nitrogen or other inert diluent through the irradiated zone, the selectivity of the reaction can be modified. By passing a continuous stream of carbon monoxide or other functionalizing gas through the reaction zone, e.g., CCl₄ or oxygen, through the irradiated zone, the starting alkane or ether substrate can be functionalized.

The equipment used to perform the photochemical reaction of this invention can be any which will irradiate the starting compound or mixture of compounds in the vapor phase, at a temperature which permits the reaction product to condense as soon as possible after it is formed and which will permit the latter to collect and remain outside the irradiated area, thereby irradiating only the starting material and not the desired product in the vapor phase. In the laboratory, this can readily be accomplished in an elongate quartz flask fitted at its top with a condensor and with a gas exit port to discharge the hydrogen produced and any other non-condensed gases. The flask is irradiated with one or more mercury vapor lamps or other source of radiant energy which converts the volatilized Group IIB metal from its ground state to an excited state, as described in the patents to Cier et al. cited above.

The substrate or substrates and a drop of Hg are poured into the bottom of the reaction chamber where they are surrounded by a variable temperature heater, e.g., a heating mantle. Although no reaction occurs in the liquid phase, liquid phase composition and temperature are critical for control of the product distribution. Varying temperature and composition allows convenient and simple control of the vapor phase concentration and composition that determines the final product distribution. For maximal reaction rate per unit volume and minimal polymerization, the substrate is refluxed and the region between the surface of the liquid at the bottom of the flask and the reflux ring at the top of the flask is irradiated. Under these conditions, dimers are rapidly swept out of the vapor phase, down the walls of the flask, and into the liquid pool where they are trapped due to their lower vapor pressure (compared to the starting compound or compounds). At the same time, the hot reflux very quickly expels the gaseous H₂ by-product from the illuminated reaction zone, which prevents the H₂ from interfering with further reaction, and allows for easy collection.

For commercial scale operation, because the radiant energy is the rate-limiting factor, it is important that escape of the radiation from the reactor is minimized. Therefore, the reaction vessel preferably surrounds the radiation source, which typically is one or more mercury vapor lamps, e.g., equipment as described in U.S. Pat. No. 2,657,985 or U.S. Pat. No. 2,830,016, modified to permit refluxing of the substrate within the irradiated area rather than passing therethrough in a single pass. The vapor pressure of the mercury can be adjusted by using an amalgam (e.g., Zn-Hg). This is useful when reactions are run at such a high temperature that the Hg vapor pressure in the irradiated zone of the reactor in which the reaction is conducted becomes so high that all of the U.V. radiation is absorbed in a very small segment of the reactor. Also, the Hg vapor can be continuously or at regular intervals metered into the reactor at a constant rate selected for optimum reactivity, when the reflux temperature of the reactor is high enough to permit Hg vapor to escape with the hydrogen exiting from the reactor, or the amount of Hg initially added to the reactor can be carefully measured so as to produce an optimum concentration of Hg vapor in the irradiated portion of the reactor.

The process can be conducted at ambient, reduced or elevated pressure, the selected pressure ordinarily being that which permits the starting substrate to reflux readily and repeatedly through the irradiated portion of the reactor. To increase reaction temperature, e.g., in the case of relatively low boiling starting substrates, or to vary the composition of the vapor phase, elevated pressures up to several atmospheres or more can be employed. To reduce reaction temperature, e.g., in the case of high boiling or readily decomposable substrates, lower pressures can be employed, e.g., water aspirator or vacuum pump pressures as low as 0.01 mm Hg or less, or the substrate can be transformed into the vapor phase by steam distillation.

The preferred metal sensitizer is mercury. The other Group IIB metals, cadmium and zinc, because they also can be volatilized, can also be employed. Other less or nonvolatile metals can be employed by providing means for exposing a large surface area thereof to the vaporized substrate, e.g., by depositing them on a high surface area substrate, such as a fine screen formed of an inert material, which is exposed to the radiant energy and which also contacts the volatilized starting substrate.

The radiant energy must consist predominantly of a frequency which is absorbed by the metal sensitizer in its ground state, i.e., its frequency must correspond to at least one of the resonance lines of the metal sensitizer, e.g., 2,537 Å in the case of Hg. Unlike the process of U.S. Pat. No. 1,961,493, which is a polymerization process, the process of this invention does not require other radiant energy sources (other than heat) or reaction catalysts in order to achieve the desired reaction. U.V. lamps are conventionally employed.

The products of the dimerization of alkanes and the relative distribution thereof can be predicted and, to a certain extent, controlled. Primary C—H bonds, i.e., a bond on a carbon atom bearing three hydrogen atoms, ordinarily will not, except under forcing conditions, react and therefore dimers formed by breaking primary C—H bonds ordinarily are not formed. Therefore, if a molecule has only primary and second centers, a statistical mix of the products of all possible secondary-secondary dimerization results, i.e., dimerization of carbon atoms initially bearing two hydrogen atoms, unless steric factors make secondary-secondary dimerization molecules extremely strained sterically, in which case primary-secondary dimerization can occur. Primary-primary dimers are never formed if a secondary or tertiary center is present in the substrate.

If the substrate alkane contains both secondary and tertiary C—H bonds, the products will be a distribution of all possible tertiary-tertiary and tertiary-secondary dimerizations. Except under forcing conditions, secondary-secondary dimerization ordinarily comprises less than five percent of the final product mixture. However, the ratio of the products of tertiary-tertiary to tertiary-secondary dimerization can be controlled by varying the reaction conditions, thereby either enhancing or limiting tertiary-tertiary dimerization. We believe the increased selectivity achievable by this invention is the result of the conversion of $^3P_1$ to $^3P_0$ Hg before reaction with the alkane substrate occurs. The critical reaction variable which enhances tertiary-tertiary selectivity is dilution of the substrate in an inert atmosphere, e.g., $N_2$, Ar, Xe, acetonitrile, $H_2O$. $N_2$ and argon lead to significant tertiary-tertiary enhancement but the best so far achieved has been in $N_2/H_2O$ atmosphere. Since $H_2O$ is inert, even as a diluent, it has obvious advantages, one of which is its ability to steam distill solids with low vapor pressures and high boiling liquids, thereby reducing the reaction temperature at which the condensation reaction must be conducted in order to maintain such a compound in the vapor phase in the reaction zone. This method rapidly brings the reaction chamber to the equilibrium vapor pressure of the alkane (or other substrate compound) and efficiently maintains this equilibrium as the condensation process depletes the supply thereof from the reaction vapor phase. Even diluents which react, e.g., methanol, promote tertiary-tertiary dimerization because of the dilution factor. Surprisingly, conducting the reaction under a vacuum, which may be mandated when the substrate has a high boiling point, can greatly suppress tertiary-tertiary dimerization. For example, the ratio of tertiary-tertiary to secondary-tertiary to secondary-secondary in the case of methylcyclohexane is about 35:62:3 in a nitrogen atmosphere and 8:87:5 in a vacuum without reflux.

The ability of $CH_3OH$ to enhance tertiary selectivity is extremely useful in the alkane functionalization process. By mixing alkanes and methanol, cross-dimerization according to this invention converts the alkane to an alcohol by hydroxyalkylation, as well as producing dimers of the alcohol and of the alkane. When the alkane has a tertiary C—H center, the cross-dimerization occurs almost exclusively at this site, even when there are ten times as many secondary C—H bonds.

The starting compounds for the process of this invention are saturated hydrocarbons (aromatics and unsaturated aliphatics suppress or kill the desired reaction and unsaturated aliphatics give complex mixtures of products), primary or secondary alcohol derivatives thereof (tertiary alcohols do not have alpha C—H bonds) and saturated hydrocarbon ethers.

The preferred saturated hydrocarbons are those having at least 5 carbon atoms, e.g., up to 25 or more carbon atoms, including alkanes and cycloalkanes, including alkyl substituted cycloalkanes, especially those having a boiling point from about 35° to about 180°, preferably about 50° to about 150°, at ambient pressure. For compounds which boil in the range of 150°–350°, a partial or high vacuum, e.g., 0.01 mm Hg or less, or steam distillation as described hereinbefore, is preferred. If a single reaction product is desired, those having a single tertiary C—H site are preferred. If a mixed reaction product is desired, those having no tertiary C—H sites and a plurality of secondary C—H sites, e.g., linear alkanes, are preferred. Those which are liquids or low melting (below 100°) solids at ambient temperature are especially preferred. Even methane and $C_2$–$C_4$ hydrocarbons undergo cross-dimerization but unless the reactor is cooled, the initial products may not condense and so trimers can be formed. For example, methane and methanol give not only EtOH but also propylene glycol from subsequent ethanol-methanol cross-dimerization.

Alcohol derivatives of saturated hydrocarbons which can be employed as starting substrates are compounds otherwise corresponding to the above-described saturated hydrocarbons which possess a primary hydroxy group as their sole functional group. Lower alkanols, e.g., methanol, ethanol, n-propanol, propanol-2, n-butanol, iso-butanol, pentanol-1, pentanol-3 and 2-methylbutanol, can also be employed preferably for the functionalization (by hydroxyalkylation) of a saturated hydrocarbon or ether thereof. The oxygen functionality is position directive and in each instance the condensation occurs on the C—H carbon atom alpha thereto. Thus, when such alcohols are employed as the major reaction substrate, the corresponding $\alpha, \beta$-glycol is the sole reaction product. When an alcohol is used to functionalize saturated hydrocarbons and ethers thereof, that glycol is ordinarily produced along with the functionalized hydrocarbon and one or more dimers thereof.

Similarly, an amino nitrogen atom is also position directing and the condensation, when it occurs, is alpha thereto. Thus, primary, secondary and tertiary alkyl and cycloalkyl amines, e.g., branched and straight chain alkylamines, dialkylamines, trialkylamines, cycloalkyl and N-alkyl cycloalkylamines dimerize at a carbon atom alpha to the amine nitrogen above. N-methylpyrrolidine condenses to N,N-dimethyl-1,1'-bipyrrolidyl isopropyl amine dimerizes to 2,3-diamino-2,3-dimethylbutane.

Ethers which can be employed as starting substrates are compounds otherwise corresponding to the above-described saturated hydrocarbons which bear an ether group as its sole substituent, e.g., symmetrical and asymmetrical dialkyl ethers, alkyl cycloalkyl ethers and cyclic ethers. The ether group, like the alcohol group, is position directing and the condensation will occur at a C—H carbon atom alpha thereto, even if it is primary C—H.

Phosphine oxide groups are similarly position directing and cause condensation at C—H group alpha to the phosphorous atom. Thus, trialkylphosphine oxides are dimerized to dialkylphosphinoethane dioxides as follows:

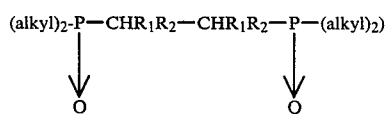

wherein alkyl is, e.g., of 1–3 carbon atoms, and $R_1$ and $R_2$ each are hydrogen or alkyl.

Alkylsilanes, dialkylsilanes and trialkylsilanes preferably wherein the alkyl is of 1–6 carbon atoms, condense at the silane atom, in a manner comparable to the dimerization of an alkane, to form a disilane.

Carbon monoxide condenses with the alkanes, ethers and alcohols described above at a 2° or 3° CH group, thereby providing a one-step synthetic route to a variety of alkane aldehydes, ether aldehyde and enediols, respectively. For example, propanol-2 and CO are converted to 2-methyl-prop-1-ene-1,2-diol, tetrahydrofuran and CO are converted to tetrahydrofurfuryl and isopropane and CO are converted to isobutyraldehyde.

Examples of specific alkanes, silanes, ethers and alcohols which can be dimerized and their dimerization products according to this invention are:

| Alkane/Ether/Alcohol/Amine | |
|---|---|
| cyclohexane | dicyclohexane; 2,2,3,4,5,5- |
| dimethylbutane | hexamethylhexane (dl-meso) |
| Isopropane | 2,2,3,3-tetramethylbutane |

-continued

| Alkane/Ether/Alcohol/Amine | |
|---|---|
| 2-methylpentane | 4,4,5,5-tetramethyloctane (33%/66%) |
| | 4,4,6-trimethyl-5-ethyl-heptane (27%/14%) |
| | 4,4,5,7-tetramethyloctane (40%/20%) |
| | (reflux/vacuum yields) |
| 2,4-dimethylpentane | 2,4,4,5,5,7-hexamethyloctane |
| 2,3,3-trimethylbutane | 2,2,3,3,4,5,6-heptamethyl-heptane (45%) |
| | 2,2,3,3,4,4,5-heptamethyl-heptane (55%) |
| 2,2,4,4-tetramethyl-pentane | 2,2,4,4,7,7-hexamethyl-6-t-butyl-octane |
| n-pentane | 4,5-dimethyloctane (25%) |
| | 3-ethyl-4-methylheptane (50%) |
| | 3,4-diethylhexane (25%) |
| tetrahydrofuran | 2,2'-dioxadicyclopentyl (dl-meso) |
| dioxane | 2,4,6,2',4',6'-hexaoxadicyclohexyl |
| methyl t-butyl ether | 2,2,7,7-dimethyl-3,6-dioxa-octane |
| diethyl ether | 2,3-diethoxy-butane |
| ethylene glycol | 3,4-dimethoxy-2,5-dioxahexane (25%) |
| dimethyl ether | 2,4,7,9-tetraoxa-octane (25%) |
| | 3-methoxy-2,5,7-trioxa-octane (50%) |
| methanol | ethylene glycol |
| ethanol | butane-2,3-diol |
| propanol | hexane-3,4-diol |
| propan-2-ol | pinacol (2,3-dimethyl-butan-2,3-diol) |
| tetrahydrofurfuryl alcohol | 1,2-di-tetrahydrofuranyl-ethylene glycol |
| ethylene glycol | 1,2,3,4-tetrahydroxybutane |
| diethylsilane | 1,1,2,2-tetraethyldisilane (one-third) |
| | "trimer" (one-third) |
| | silane polymer (one-third) |
| N—methylpyrrolidine | N,N'dimethyl-2,2'-bipyrrolidyl (80%) |
| | 2-(1-azacyclopentylmethyl)-N—methyl-pyrrolidine (20%) |

Examples of alkane/ether, silane/ether, silane/alcohol, silane/alkane, alkane/alcohol and ether/alcohol mixtures which condense to form dimers according to this invention are:

| Mixture | Products |
|---|---|
| tetrahydrofuran/2-methylpentane | 2,2'-dioxadicyclopentyl-2'-2-(2-methyl-pentyl)-tetrahydrofuran 4,4,5,5-tetramethyl-octane |
| tetrahydrofurfuryl methanol | ethylene glycol tetrahydrofurfyl alcohol 2,2'-dioxadicyclopentyl |
| 2,3,3-trimethyl-butane/methanol | 2,2,3,3-tetramethylbutan-1-ol ethylene glycol 2,3,3,5,5,6,6-heptamethylheptane 2,2,3,5,5,6,6-heptamethylheptane 2,2,3,3,4,4,5,5-octamethylhexane (11:05:1:1:4 ratio) |
| 2,4,4-trimethyl-pentane/methanol | 2,2,4,4,5,5,7,7-octamethyloctane, ethylene glycol, 2,2,4,4,-tetramethyl-1-pentanol |
| cyclohexane propan-2-ol | 2-cyclohexyl-propan-2-ol pinacol dicyclohexyl |
| 2-methylpentane propan-2-ol | 2,2,3,3-tetramethyl-pentanol pinacol 4,4,5,5-tetramethyloctane |
| triethyl silane/methanol | hexaethyldisilane, ethylene glycol hydroxymethyltriethylsilane |
| 1,3,5-trioxolane/cyclohexane | bicyclohexyl 2,4,6,2',4',6'-hexaoxybicyclohexyl 2,4,6-trioxybicyclohexyl (which can be hydrolyzed to cyclohexylaldehyde with acid) |
| triethylsilane/cyclohexane | hexaethyldisilane bicyclohexyl cyclohexyltriethylsilane |

-continued

| Mixture | Products |
|---|---|
| triethylsilane/diethyl ether | 1-ethoxyethyltriethylsilane hexaethyldisilane 2,3,diethoxybutane |
| pyrrolidine/methanol | 2-hydroxymethylpyrrolidine glycol N,N'—dimethyl-2,2'-bipyrrolidyl |

The products of this invention are useful for the purposes which would be obvious from their structure. For example, the hydrocarbon dimers are useful as fuels and lubricants, and the alcohols and glycols as chemical intermediates, solvents, emollients, greases, and the glycols are useful vehicles for cosmetics. Some of the products are novel compounds because of the difficulty of preparing them by other chemical synthetic methods, one of them being the dimer produced from 2,2,4,4-tetramethylpentane. Another is 2,2,4,4-tetramethylpentanol, which can be produced inexpensively from isooctane (2,4,4-trimethylpentane) and methanol and converted easily by catalytic hydrogenation to 2,2,4,4-tetramethylpentane. 2-Methylheptanol, 2-ethylhexanol and 2-n-propylpentanol, which are produced from n-heptane and methanol, are useful known compounds. For example, 2-ethylhexanol is used for mercerizing textiles and as a solvent for dyes, resins and oils. Cyclohexylcarbinol, produced by cross dimerization of cyclohexane and methanol, is the subject of U.S. Pat. No. 2,940,913. Ditetrahydrofuran, produced by dimerizing tetrahydrofuran, is useful in a manner comparable to triglyme. I-cyclohexylethanol, produced by the cross-dimerization of cyclohexane and ethanol, can be oxidized conventionally to cyclohexyl methyl ketone, which is used in air freshener aerosols. See Chem. Abstr. 89:117570g., German Offen. No. 2,756,050. Other cyclohexyl alkyl ketones of these references can also be similarly prepared according to this invention. Organo-silicon compounds, e.g., 1,1,2,2-tetraethyldisilane is useful for electrophotographic imaging materials. See Chem. Abstr. 102:729451v, Japan Kokai Koho JP No. 60-32,055; Japanese Application No. 83/142,208; Chem. Abstr. 102:123069m, Ger. Offen. DE No. 3,415,620; JP Appln. No. 83/75,270. A wide variety of flavors and fragrances can be produced according to this invention. For example, 2,2,5,5-trimethyl-4-isopropyl-1,3-dioxane, which has a lavender odor and is used to perfume soaps, can be produced by cross-dimerizing 2,2,5,5-trimethyl-1,3-dioxane with propane. Other alkanes and dioxanes, produced by forming cyclic ketals from various 2,2-dialkyl-1,3-propylene glycols and dialkyl ketones, can be used to produce similarly useful homologues. The process of this invention is thus particularly useful for producing higher alkanes having a sterically highly hindered carbon atom.

Contemplated equivalents of the saturated hydrocarbons, alcohols thereof and ethers thereof which can be employed in the process of this invention are those having one or more non-reactive substituents, e.g., cyano, fluoro and trifluoromethyl. For example, 2,2,2-trifluoroethanol and 2,2,2-trifluoroethylether are dimerized to 1,1,1,4,4,4-hexafluorobutan-2,3-diol and the trifluoroethyl diether of 1,1,1,4,4,4-hexafluorobutan-2,3-diol, respectively. The former compound can be converted by standard chemical routes to perfluoro-2-butyne, which is well known as an exceptional Diels-Alder dienophile. This alkyne can also be converted to polymers useful for a variety of commercial products, e.g., highly hydrophobic coatings. See Chem. Abstr. 55:8916e; U.S. Pat. No. 2,966,482. As stated above, interfering groups, such as phenyl and naphthyl, must not be present.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

In all of the examples which follow, unless indicated otherwise, the selected starting compound or mixture of compounds was placed in the bottom of a 1600 ml quartz reaction vessel along with a drop of mercury, and a stir bar. The reaction vessel was flushed with nitrogen, capped with a 24/40 joint equipped with an open stopcock, placed on a heating mantle and a magnetic stirrer and placed inside a photoreactor equipped with four 8-watt, low pressure 254 nm. mercury lamps. The starting compound was brought to a gentle boil, at a temperature which permitted the starting compound or compounds to condense above the irradiated zone but well below the boiling point of the reaction product. The refluxing was continued for about 24 hours or until refluxing ceased, in the case of an alkane, ether, alcohol or trialkylsilane.

When functionalizing an alkane or ether (having a boiling point between 60° and 100°) with methanol or ethanol, the refluxing was continued for 2 or 3 days. Fractional distillation, with or without simple extraction techniques with polar and non-polar solvents, permits easy separation of the alkanic, alcoholic and glycol reaction products.

When functionalizing with carbon monoxide, a stream of the latter was flushed through the refluxing alkane or ether and allowed to exit from the apparatus along with the hydrogen by-product. This procedure can be used to enhance the formation of 3°–3° dimeric product, e.g., by bubbling $N_2$, $H_2O$, acetonitrile, argon, xenon or other non-reactive compound below the surface of the boiling alkane or ether during the period of irradiation. This procedure can also be used to functionalize a higher boiling (above 110°) alkane or ether with methanol or other alkanol or where dimerizing a mixture of compounds having widely diverse boiling points, e.g., bubble a stream of the volatilized alkanol below the surface of the boiling starting material in the bottom of the reactor. The unreacted alkanol can be recovered from the exiting gases when passing them through a water cooled condenser.

In the preceding text and the following examples, all temperatures are set forth uncorrected in degrees Celsius and all parts and percentages are by weight, unless otherwise indicated.

EXAMPLE 1

Bicyclohexyl

28 Gms. of cyclohexane were brought to a very gentle reflux in the equipment described above and the lights were turned on for four days. The thus-produced crude bicyclohexyl was removed from the reaction vessel and, after vacuum distillation, yielded 26.2 Gms. (94%) of bicyclohexyl plus 1.6 Gms. (6%) oligomers. 250 MHz $^{13}$C NMR (CDCl$_3$) 43.69(d,2C), 30.42(t,4C), 27.11(5,2C), 27.09(t,4C).

EXAMPLE 2

2,2,5,5,7,7-Hexamethyl-(3-dimethylethyl)octane

10 Gms. of 2,2,4,4-tetramethylpentane were brought to the boiling point and photolyzed for 24 hours in the apparatus described above. The alkane was completely consumed, yielding, after vacuum distillation, 9.2 Gms. of liquid dimers which, by examination by GC, consisted of 95% of the desired product. 250 MHz $^{13}$C NMR (CDCl$_3$) 3 quartets; 31.05, 32.44, 32.56; 2 triplets; 40.96, 59.42; doublet; 51.83; 3 singlets: 34.83, 35.48, 36.57. 250 MHz $^1$H NMR (CDCl$_3$) 1.41(d,2H), 1.31(s,2H), 1.19(t,1H), 1.0(s,9H), 0.99(s,18H), 0.95(s,6H).

EXAMPLE 3

1,1', 4,4'-Tetramethylbicyclohexyl

5 Gms. of 1,4-dimethylcyclohexane were brought to a gentle boil in the equipment described above and photolyzed for 24 hours. The 5 Gms. of dimers are removed from the flask and taken up in an equal volume of ether. When placed in a freezer at −20 degrees, 1 Gm. (20%), of the desired product crystallizes out of solution. 250 MHz $^{13}$C NMR (CDCl$_3$ 16.59(q,2C), 17.43(q,2C), 24.07(t,4C), 27.73(t,4C), 26.71(d,2C), 38.45(s,2C). 250 MHz $^1$H NMR (CDCl$_3$) 1.87(m,2H), 1.66(t,8H), 1.30(d,4H), 1.05(d,4H), 0.93(d,6H), 0.87(s,6H).

EXAMPLE 4

Ethane-1,2-diol di-tert-butyl ether

20 Gms. of tert-butyl-methyl ether were brought to reflux in the equipment described above. The vapor phase was photolyzed overnight. The reaction mixture was rotovapped down to 10 Gms. of dimer. Vacuum distillation yielded 9.5 Gms. of the pure dimer. 250 MHz $^{13}$C NMR (CDCl$_3$) 1.13(s,18H), 3.41(s,4H).

EXAMPLE 5

3,3,6-Trimethyl-2-heptanol

A mixture of 10 Gms. of ethanol and 10 Gms. of 1,4-dimethylhexane were warmed to approximately 90 degrees and photolyzed for 48 hours in the equipment described above. The product was removed and taken up in an equal volume of ether. The ethylene glycol was washed out of the ether solution with 3 small portions of water. The ether was then removed and the residual alkane/alcohol mixture was taken up in an equal volume of methanol, which was then washed in a separatory funnel with 4 or 5 minimal portions of hexanes. Water was added when necessary to resolve the hexane layer. The accumulated hexane portions were then backwashed with 2 equal portions of methanol. The combined methanol layers were evaporated under vacuum to yield 7.5 Gms. of the crude alcohol. $^{13}$C NMR (CDCl$_3$ 5 quartets; 23.99, 22.40, 22.36, 22.23, 17.31; 2 triplets: 32.56, 36.16; 2 doublets: 73.90, 28.59; singlet; 36.85.

EXAMPLE 6

Hexaethyldisilane

Triethylsilane (15 g) was heated at 100° and irradiated for a 24 hours period in the equipment described above. At the end of this period, the material remaining in the reactor is essentially pure hexaethyldisilane, as shown by the $^{13}$C NMR and $^1$H NMR. $^1$H NMR (position (δ), multiplicity (t=triplet, q=quartet, etc.), assignment): 1.02(t,Me), 0.69, (q, CH$_2$) $^{13}$C NMR (off resonance decoupled); 4.12, t, CH$_2$, 8.24, q CH$_3$.

EXAMPLE 7

Reaction of Cyclohexane with CO

Cyclohexane (5 g) was flushed with CO and irradiated at room temperature for 16 hours in the equipment described above. The liquid in the reactor was then removed and the unreacted cyclohexane evaporated therefrom in a rotary evaporator. The residue (3 g) was examined and found to contain bicyclohexyl (1.5 g, determined by comparison of the $^1$H NMR with that of authentic material), cyclohexylaldehyde (0.7 g, determined by GC retention time, IR spectroscopy and $^1$H NMR by comparison with an authentic sample; the CHO resonance at 9.62 being the characteristic feature of the NMR); and a third product (0.7 g), which also had a C—O IR vibration and probably is dicyclohexyl ketone.

EXAMPLE 8

Hexadecane Dimers

Hexadecane (200 g) was strongly refluxed under reduced pressure for four days in the equipment described above, whose gas outlet was fitted to an aspirator. Upon distillation, the crude product yielded hexadecane (140 g), a mixture of hexadecane dimers (58 g) and a residue of higher molecular weight material (2 g). The dimer fraction showed no vinyl C$\underline{H}$ resonances in the $^1$H NMR, showing that the amount of alkene was less than 1%, a result confirmed by Mass Spectroscopy, which also showed that all the dimer fraction had a mol. wt. corresponding to the presence of 32 carbons and not other numbers. The $^{13}$C and $^1$H NMR of the product is consistent with a mixture of branched chain materials. Based on the results obtained with lower mol. wt. C$_5$ and C$_6$ linear alkanes, where essentially no 1°—1° or 1°—2°. dimers are formed and the only observable products are 2°—2° dimers, the thus-produced dimers of hexadecane are believed to be all of the R$^1$R$^2$CH—CHR$^3$R$^4$ type where R$^1$-R$^4$ are linear alkyl chains, and the length of the chains is such that the length of R$^1$ plus the length of R$^2$ plus one equal 16 and R$^3$+R$^4$+1 equal 16.

EXAMPLE 9

Dimerization of methylcyclohexane under conditions which alter the ratio of 2°-3° to 3°—3° products.

Method A (designed to maximize 2°-3° products):

Methylcyclohexane (30 g) was strongly refluxed in the equipment described above for 24 hours. The product was then distilled to give a dimer fraction (10 g). The GC, $^{13}$C and $^1$H NMR show that the dimeric products are 90% 2°-3° and 10% 3°-3° (1,1'-dimethylbicyclohexyl). The 2°-3° product is a mixture of all of the six possible dimeric isomers.

Method B (designed to maximize 3°—3° products):

Methylcyclohexane (8 g), in the equipment described above, was not heated but allowed to establish its own vapor pressure throughout the vessel, which therefore still contained largely N$_2$ which acted as a diluent gas. The GC, $^{13}$C and $^1$H NMR of the crude product shows that the dimeric product was 60% 2°-3°dimer and 40% 3°—3° dimer. The 3°—3° product could be crystallized from the mixture by diluting the dimer fraction 1.1 with Et$_2$O and cooling to −80° C. for 24 hours to give 3 g of pure, crystalline product (m. pt, 43° C.). $^{13}$C NMR; 16.6, q, CH$_3$; 22.4 and 30.35, t, 2— and 3—CH$_2$; 26.6, t, 4-C; 38.14, s, 4° C.

EXAMPLE 10

Pinacol 30 gm of isopropanol were placed in the bottom of a 1600 ml quartz reactor along with a drop of mercury. The vessel was placed on a heating mantle inside a Rayonet Photoreactor equipped with four 8 watt low pressure mercury lamps. The heating mantle was turned on and adjusted so that the reflux ring reached the top of the reaction vessel. The system was photolyzed overnight. The reactor was emptied and the unreacted isopropanol evaporated. 3 gms of pinacol were produced. It could be easily recrystallized from water.

EXAMPLE 11

Cyclohexydimethylcarbinol 20 gm of cyclohexane and 20 gm of isopropanol were treated as in Example 10. The product is a mixture of alkane, alcohol, and glycol. The glycol is separated by taking the crude product up in hexanes and washing with water. The alcohol is separated from the alkane by distillation.

EXAMPLE 12

1,1,2,2 tetramethylpentanol 30 gm of isopropanol and 8 gm of 2 methylpentane were treated as in Example 10. The product is a mixture of alkane, alcohol and glycol. The glycol is removed by washing the crude product with water and the alcohol separated from the alkane by distillation. This procedure yields approximately one gm of alcohol.

EXAMPLE 13

Steam Distillation 40 gm of tetradecane were placed in the bottom of 1600 ml quartz reactor along with 30 ml of water and a drop of mercury. The quartz flask was then placed inside a Rayonet photoreactor equipped with four 8 watt low pressure 254 nm U.V. lamps. The water was brought to a reflux and then the reactor lamps were ignited. After six hours of illumination distillation of the alkane fraction yielded 6 gms of dimers.

EXAMPLE 14

1,2-trifluoromethylethylene glycol 25 grams of trifluoroethanol and a drop of mercury were placed in the bottom of a 1600 ml quartz flask. The flask was placed in a Rayonet photoreactor equipped with four 8 watt low pressure 254 nm U.V. lamps. The trifluoroethanol was brought to a reflux before turning on the reactor. After 16 hours of illumination distillation yielded 11 gm of dimer evenly split between dl and meso. One of the dimers is a crystalline solid at room temperature which is insoluble in dichloromethane. This allows for easy separation from the other isomer.

EXAMPLE 15

Trifluoroethylether dimers

When 2 gm of trifluoroethyl ether were treated by the same conditions as in Example 14, except at 40° C.

under nitrogen instead of at reflux, complete conversion to dimer was obtained overnight. The product is 50—50 dl and meso.

EXAMPLE 16

1,1,2,2-tetraethyldisilane

When 5 gm of diethylsilane were treated to the same conditions as the trifluoroethylether, complete conversion to high dimer and polymer was obtained overnight. Distillation of the product yielded 1.8 gm of 1,1,2,2-tetraethyldisilane, 1.0 gm of "trimer" (the analysis is uncertain), and 2.2 gm of nondistillable polymer.

EXAMPLE 17

Dimethylphosphinoethane dioxide 1 gm of trimethylphosphine oxide was dissolved in 2 mls of distilled water. The solution was placed in an 18 ml tube and brought to reflux inside the Rayonet reactor. When reflux was reached the lights were turned on. After several days of photolysis the oxide is completely converted to its dimer. Reduction of the dimer in a conventional manner produces 1,2-bis(dimethylphosphino)ethane.

EXAMPLE 18

N,N'-dimethyl-1-1'-bipyrrolidyl 25 gm of N-methylpyrrolidine were placed in the bottom of a 1600 ml quartz reactor with a drop of mercury. The reactor was then placed on a heating mantle inside a Rayonet photoreactor equipped with four 8 watt low pressure 254 nm U.V. lamps. The pyrrolidine was brought to a gentle boil and irradiated. After 24 hours illumination the solution was removed from the quartz flask and the starting material removed by distillation. 10 gm of product remained of which 75% was the named product and 25% was 1-methyl-2-pyrrolidino-pyrrolidine.

EXAMPLE 19

2,3-diamino-2,3-dimethylbutane 25 gm of freshly distilled isopropyl amine were treated as above. After distillation 2 gm of sticky crystalline material remained. Room temperature sublimation yields 1.5 gm of clear crystals of the named product.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modification of the invention to adapt it to various usages and conditions.

What is claimed is:

1. A method of improving at least one of the selectivity and space-time yield of a Group IIB photosensitized vapor phase dimerization, which comprises dimerizing a gaseous mixture of (a) a Group IIB metal and (b) a saturated hydrocarbon secondary alcohol, or a mixture of either a saturated hydrocarbon or a saturated hydrocarbon ether, and a saturated hydrocarbon secondary alcohol, at a reaction temperature at which the reaction product condenses immediately upon the formation thereof and remains condensed while exposed to the photosensitizing radiant energy.

2. The method according to claim 1, wherein the starting material contains at least 6 carbons atoms.

3. The method according to claim 1, wherein the starting material is a mixture of saturated hydrocarbon secondary alcohol and the reaction product comprises a cross-dimer thereof.

4. The method according to claim 1, wherein the starting material comprises a primary alcohol.

5. The method according to claim 1 wherein the starting material is a mixture of a saturated hydrocarbon secondary alcohol and a saturated hydrocarbon ether and the reaction product comprises a cross-dimer thereof.

6. The method according to claim 1, wherein the Group IIB metal is mercury and the dimerization is photosensitized by a resonance frequency radiation of a wavelength of 2,537 Å.

7. The method according to claim 1, wherein the starting material is refluxed into a reaction zone which is irradiated with photosensitizing radiant energy and is thereby exposed repeatedly thereto.

8. The method according to claim 1, wherein the Group IIB metal is mercury and the dimerization is photosensitized by a resonance frequency radiation of a wavelength of 2,537 Å; and wherein the starting compound is refluxed into a reaction zone which is irradiated with photosensitizing radiant energy and is thereby exposed repeatedly thereto.

9. The method according to claim 1, which comprises conducting the dimerization in the presence of a non-reactive gas.

10. The method according to claim 9, wherein the non-reactive gas is nitrogen.

11. The method according to claim 9, wherein the non-reactive gas is volatilized $H_2O$.

12. The method according to claim 9, wherein the vapor phase molar ratio of non-reactive gas to starting saturated hydrocarbon in the reaction zone is from about 1:10 to about 100:1.

13. A method for the hydroxyalkylation of a volatilizable saturated hydrocarbon or an ether thereof, which comprises subjecting a gaseous mixture of the hydrocarbon or ether thereof, a secondary alkanol and a Group IIB metal, to an amount of radiant energy comprising a frequency which can be absorbed by the metal at its ground state effective to condense the alkanol with the hydrocarbon.

14. The method according to claim 13, wherein the starting material is an alkane or mixture of alkanes.

15. The method according to claim 13, wherein the Group IIB metal is mercury and the dimerization is photosensitized by a resonance frequency of a wavelength of 2,537 Å.

16. A method according to claim 13, wherein the vapor phase molar ratio of the hydrocarbon or ether thereof to the alkanol is from about 10:1 to about 1:10.

17. A process for the production of a 1,2-bis(dialkylphosphino)ethane dioxide, which comprises irradiating a gaseous mixture of a volatilizable trialkylphosphine oxide, wherein at least one of the alkyl groups has a hydrogen atom on the carbon atom thereof alpha to the phosphorous atom, and a Group IIB metal with an amount of radiant energy comprising a frequency which can be absorbed by the metal at its ground state effective to dimerize the phosphine oxide.

18. The method according to claim 17, wherein the Group IIB metal is mercury and the dimerization is photosensitized by a resonance frequency radiation of a wavelength of 2,537 Å.

19. A one-step process for the production of an aldehyde which comprises irradiating a gaseous mixture of a Group IIB metal, carbon monoxide and a saturated hydrocarbon, a saturated hydrocarbon ether, a saturated hydrocarbon primary or secondary alcohol, or a mixture thereof, at a reaction temperature a which the reaction product condenses immediately upon the formation thereof and remains condensed while exposed to the photosensitizing radiant energy.

20. The method according to claim 19, wherein the reactants are carbon monoxide and a saturated hydrocarbon.

21. A process for the production of a fluorinated glycol which comprises irradiating a gaseous mixture of a volatilizable fluorinated alcohol of the formula $R_1CH_2OH$, wherein $R_1$ is a perfluoroalkyl group, and a Group IIB metal in the presence of photosensitizing radiation so as to dimerize the fluorinated alcohol.

22. The method according to claim 21, wherein the Group IIB metal is mercury and the dimerization is photosensitized by a resonance frequency of a wavelength of 2,537 Å.

23. A method of improving at least one of the selectivity and space-time yield of a Group IIB photosensitized vapor phase dimerization, which comprises dimerizing a gaseous mixture of (a) a Group IIB metal, (b) a saturated hydrocarbon or a saturated hydrocarbon ether and (c) 1,3,5-trioxane, at a reaction temperature at which the reaction product condenses immediately upon the formation thereof and remains condensed while exposed to the photosensitizing radiant energy to produce a reaction product which comprises a cross-dimer thereof.

24. A method of improving at least one of the selectivity and space-time yield of a Group IIB photosensitized vapor phase dimerization, which comprises dimerizing a gaseous mixture of a Group IIB metal, a saturated amine and 1,3,5-trioxane, at a reaction temperature at which the reaction product condenses immediately upon the formation thereof and remains condensed while exposed to the photosensitizing radiant energy, to produce a reaction product which comprises a cross-dimer thereof.

* * * * *